United States Patent [19]

Pikul

[11] 4,122,842
[45] Oct. 31, 1978

[54] PULMONARY DIAGNOSTIC INSTRUMENT INCLUDING BREATH TRANSDUCER

[75] Inventor: Richard E. Pikul, DeSoto, Mo.

[73] Assignee: Puritan Bennett Corporation, Kansas City, Mo.

[21] Appl. No.: 649,986

[22] Filed: Jan. 19, 1976

Related U.S. Application Data

[62] Division of Ser. No. 495,329, Aug. 7, 1974, Pat. No. 3,946,726.

[51] Int. Cl.² .............................................. A61B 5/08
[52] U.S. Cl. ...................................... 128/2.08; 73/228
[58] Field of Search ...................... 128/2.08, 2.07, 2 C, 128/DIG. 29; 272/99; 73/194 E, 228

[56] References Cited

U.S. PATENT DOCUMENTS

| | | | |
|---|---|---|---|
| 2,769,337 | 11/1956 | Rich | 73/228 X |
| 2,907,320 | 10/1959 | Weese et al. | 128/DIG. 29 X |
| 3,119,262 | 1/1964 | Wright et al. | 73/228 |
| 3,164,990 | 1/1965 | Henness et al. | 73/228 |
| 3,232,288 | 2/1966 | Krobath | 128/2.08 |
| 3,494,190 | 2/1970 | Schwartzman | 73/228 |
| 3,528,288 | 9/1970 | Scoortes | 73/194 E X |
| 3,680,378 | 8/1972 | Aurilio et al. | 128/2.08 X |

FOREIGN PATENT DOCUMENTS

| | | | |
|---|---|---|---|
| 1,171,631 | 6/1964 | Fed. Rep. of Germany | 73/228 |
| 2,241,095 | 3/1974 | Fed. Rep. of Germany | 73/228 |

*Primary Examiner*—Lee S. Cohen
*Attorney, Agent, or Firm*—Paul M. Denk

[57] ABSTRACT

In a pulmonary diagnostic instrument that includes a breath transducer for use in conjunction with the instrumentation for detecting respiratory functioning of a patient or specimen, the transducer comprises a flow tube in which is suspended for lineal displacement a partial diaphragm generally constructed as a foraminous plate, and which during testing, the specimen's breath flows therethrough to achieve some degree of displacement of said diaphragm. The diaphragm incorporates and operates in association with various ferrous rings for enhancing the transfer of magnetic lines of flux which are generated by a charged E-core for determining the extent of said lineal displacement which is representative of and can be interpreted to provide information pertaining to pulmonary functioning for diagnosis of the respiratory system of the specimen. In another embodiment charged capacitive plates replace the aforesaid ferrous rings and E-core, and through a developed capacitive imbalance caused by the breath induced diaphragm displacement providing information that may be interpretive of pulmonary functioning, or flow of air.

11 Claims, 13 Drawing Figures

PULMONARY DIAGNOSTIC INSTRUMENT INCLUDING BREATH TRANSDUCER

This application comprises a division of the prior application having Ser. No. 495,329, as filed on Aug. 7, 1974, now U.S. Pat. No. 3,946,726.

BACKGROUND OF THE INVENTION

This invention relates generally to instrumentation for pulmonary diagnosis, and more particularly pertains to a breath transducer functioning under the force of specimen breath to provide lineal displacement of its diaphragm for allowing diagnosis of the specimen's lungs and a possible detecting of early signs of pulmonary disorders.

Various types of pulmonary diagnostic instruments have long been available upon the market for use as a means for broadly testing for respiratory dysfunction of persons who are believed to be inflicted with some form of respiratory impairment. Instrumentation of this nature appears to be one expediency available to the medical profession as a means for detecting such disorders, since any such disease or obstruction somewhere within the remote confines of the lung are difficult of detection, do not provide any form of direct manifestation of existence, and do not lend themselves to any form of probe for direct analysis, and hence, such difficulty of detection originally led to the various forms of tests that could be conducted upon the respire of breath as a means for sensing an indication of what perhaps might be a lung disfunction.

Any analysis of lung disease, heretofore, in this manner, for those forms of disease which lead to chronic airway obstruction, is generally recognized by the profession as one of the most important and yet frustrating health problems in existence, with the treatment of such diseases being particularly frustrating because by the time the patient usually seeks medical assistance, such as due to the physical manifestation of his shortness of breath, or the like, or because some form of diagnostic test has finally revealed an abnormal pulmonary function, the disease is generally to that stage of development that it has become incurable. Part of this problem is due to the fact that present pulmonary diagnostic instruments are not sufficiently sensitive enough to provide an early warning of incipient diseases of the lung, but rather, such present instrumentation exhibit a rather wide variance of tolerance limits in their measurements that are really of very little assistance to the pracititioners in their attempts to practice preventative type medicine for at least an early curtailment of any beginning lung disease.

Reportedly, among the most useful of pulmonary examinations that is currently receiving some attention as a means for detecting potential or developing disease of the lungs is the measurement for closing volume of the lungs during functioning of one's respiratory system. Closing volume has generally been defined as a measurement which may perhaps detect respiratory disease in its preclinical stages. It is the lung volume during expiration over which emptying of the dependent regions of the lung is severely reduced or ceases altogether. A certain amount of closing volume exists in most individuals, with the capacity for closing volume gradually increasing with age, a phenomenon that is thought to exist and occur due to the changes in the lung elastic recoil over a lifetime. Hence, certain standarized forms of information are available regarding closing volume, and which can and do establish the health parameters for individuals with normal pulmonary functioning. On the other hand, persons that have either definite lung disease, or those that subject themselves to excessive tobacco smoking, exhibit changes generally of detrimental form in the measurement of their closing volumes which may give a ready indication that airway obstruction is developing or has long developed, and perhaps is amplifying to dangerous levels, so that the physician knows that disease is present and a medical reality in the lungs.

Medical authors have expressed the opinion that existing pulmonary devices are not accurate enough to provide the type of information that is needed for diagnosis of early airway diseases, but state that if such tests could be conducted upon instrumentation that would function sensitive and precision enough, then perhaps lung related diseases could be detected at their much earlier stages of development and lead to much more effective if not preventative treatment. Hence, sensitive instrumentation would be useful to provide patient pulmonary analysis on a much more great scale, and could even be used as a screening program for testing whole masses of people, and through the utilization of such sensitive test results, and their comparison with known health parameters, provide the medical examiner with sufficient information for determining whether any one individual tested may possibly be developing incipient lung and airway disease. Hence, such sensitive tests, including closing volume, could probably detect early lung damage, and possibly at a stage when it is still totally reversible.

Various types of pulmonary devices are presently available upon the market, and generally operate under a variety of principles to achieve breath analysis for determining, particularly, the closing volume of the lung in addition to other pertinent information. Such devices, as previously analyzed, have been of questionable accuracy, but in any event, they generally incorporate various types of spirometric instrumentation for analyzing the air respiring from the lungs. Such tests, more specifically, may provide an analysis of the nitrogen washout, including closing volume, vital capacity, and other lung air flow volumes of breath, and the information obtained from these tests is useful for providing some basis for medical analysis of the patient. Such devices may include the Expirometer as presently marketed by the Warren E. Collins, Inc., of Braintree, Massachusetts. The spirometer functions under the principle of rotating turbine blade means to reflect a light on a photo-transistor for producing pulses that are counted by digital logic for yielding a direct volume readout of pulmonary flow rate. The Spirostat is a turbinometer, having bi-directional measuring attibutes, and which measures the rotational speed of turpine like vanes which is proportional to the flow of the specimen breath. This device is manufactured and marketed by Fibre-O-Optics Industries, Inc., of West Palm Beach, Florida. Other forms of prior art pulmonary analyzing devices include the Pulmonary Functioning Indictor, as manufactured and sold by Chemetron Corporation, of Chicago, Illinois, and the Pulmonary Function Analyzer, as marketed by the Monaghan Company of Denver, Colorado. Both of these two latter devices incorporate a thermistor, either of the hot wire type or the trimetallic bead type, which when cooled by expired breath provides a read out of information relating to lung volume and breath flow.

The problems with many of these prior art spirometers is accurately described in the *New England Journal of Medicine,* Volume 289, No. 24, commencing on page 1283, and entitled "Evaluation of Electronic Spirometers", by FitzGerald, Smith, and Gaensler. For example, in a test using the Spirometer for determining maximum voluntary ventilation, the subject instrument underestimated this measurement on the average of 44 percent. The Pulmonary Function Analyzer underestimated by 21 percent the true measurement for maximum voluntary ventilation during the instrument evaluation. In their evaluation of these instruments for their effectiveness in measuring the forced vital capacity of the subjects being tested, the Pulmonary Function Indicator recorded volumes that were 20 to 50 percent high. The Spirostat recorded accurate volumes only at rapid flow rates, but that when its syringe emptying time exceeded two seconds, the volume was seriously overestimated. In the forced expiratory volume in one second test, the Pulmonary Function Indicator showed almost random scatter of measurements, with values deviating from the expected by as much as plus 40 percent to a minus 85 percent. In forced vital capacity tests, the Expirometer recorded readings as much as sixteen percent over what the reading should have been, and it was determined that this occurs in the turbinometer type of instrument due to the inability of vane type meters to quickly change their velocity during uneven breath flow type tests.

Such deviations in measurements of pulmonary function provide information that certainly cannot be utilized by the practitioner with any confidence as a means for determining the presence of pulmonary disease, particularly at an early stage. As the authors' state in the aforesaid article: "The increasing prevalence of chronic obstructive lung disease underlines the importance of screening of ventilatory function in the physician's office, in the clinic, and at the bedside." But that unless the present instruments "... are accurate and stable in the clinical context their general use may prove misleading in individual cases and eventually may discredit screening procedures of proved value." They summarize that the permissible range of deviation of plus or minus five percent from the primary standard is needed to observe the course of disease or the effect of drugs in an individual patient. "Electronic spirometers offer sufficient convenience advantages to justify further development. The instruments that we examined would not be recommended in their present form because of insufficient accuracy and because three lacked facilities for calibration. Furthermore, convenience advantages are offset by high cost and lack of permanent record without expensive accessory equipment."

One other instrument is presently and commonly used for measuring the velocity of respiratory air currents. This device is entitled the Pneumotachograph, and is sold by Instrumentation Associates of New York, New York. This device operates upon the principle of passing the breath through a plurality of small diameter ducts, being approximately 0.8 mm. in diameter and 32 mm. in length. And, the instrument then measures the pressure differential between the air entering the series of ducts, and that leaving said ducts, and the measurement of this pressure drop providing a reading as to the representative velocity of expired breath. One advantage of utilizing this type of a pressure drop or differential measurement is that it is much more responsive instantaneously to the exact quantity and velocity of the passing breath, but one draw back is that it is difficult to control the conversion of such measurements to representative values of breath flow so as to provide accuracy in read out, and this is due mainly because there is no physical manifestation of this pressure differential that can be easily detected and gauged by supporting mechanism. In addition, this prior art instrument is quite elaborate of structure, and expensive of cost.

Hence, in view of the foregoing, it can be stated effectiveness, accuracy, and reliability of diagnostic equipment is just as important to patient welfare as the effectiveness, precise dosage, and purity of administered drugs. The need for instrumentation to provide accurate pulmonary diagnosis is readily apparent from the measurements and testing that has been made upon existing prior art devices.

It is, therefore, the principal object of this invention to provide a pulmonary diagnostic instrument and its accompanying transducer which operates upon the principle of lineal displacement of its partial diaphragm to provide accurate measurements respresentative of information that may provide a determination of the closing volume of a specimen, in addition to other forms of related types of preliminary measurements.

It is another object to provide a pulmonary diagnostic instrument which is sufficiently sensitive to provide precise measurements regarding lung operation, and for furnishing more definite information for the physician to make early detection of potential and beginning lung disease.

It is a further object of this invention to provide a pulmonary instrument including a breath transducer that achieves a reproducible line or lineal displacement of its suspended diaphragm in direct relation to the force of movement, or flow rate, of the specimen breath therethrough, with the displacement being detected, gauged, and correlated to provide direct readout of information for lung analysis.

It is an additional object of this invention to provide a breath transducer for a pulmonary diagnostic instrument that functions to provide very sensitive and accurate information pertaining to the closing volume of a patient being screened.

Another significant object of this invention is the provision of a breath transducer for a diagnostic instrument which is replaceable and disposable.

A further object of this invention is to provide a mouthpiece transducer for a diagnostic instrument which can be quickly and promptly inserted or removed from its holder to facilitate its prompt usage and disposal.

Another object of this invention is to provide a breath transducer incorporating a lineal displacement suspension diaphragm which maintains a standard of tolerance consistently within, or less than, a plus or minus five percent from the normal.

An additional object of this invention is the provision of a breath transducer that is disposable and thereby eliminates the possibility of communication of disease from one patient to another.

A further object of this invention is to provide a breath transducer for a diagnostic instrument that can be used for measuring and performing the standard closing volume tests, in addition to other forms of pulmonary tests generally administered by physicians, such as the nitrogen wash-out measurement.

Another object of this invention is to provide a breath transducer, and its associated diagnostic instrument holder, which are facile of manufacture, inexpensive in cost, and which lend themselves to assembly line manufacture.

SUMMARY OF THE INVENTION

This invention contemplates the use of a suspended sensitive partial diaphragm which upon encountering the flow of breath enters into a degree of lineal displacement which is detectable and measurable to provide readings that can be electronically converted to furnish direct information relating to the functioning of the pulmonary system of a patient. Such information, as previously analyzed, and if of sensitive scope, can provide the physician with needed information for determining early signs of lung disease. As also previously analyzed, prior art devices of this nature are too insensitive and exhibit too great a tolerance for error, and therefore, can only be used in general screening tests of large numbers of people as a means for only detecting disease when it has become a major detriment to the patient itself, and in most cases has already reached the irreversible stage. Heretofore, various types of prior art breath analyzers have established the normals and averages for pulmonary functions for great masses of patients and populations, with said information having been derived over long periods of time. These measurements have led to the charting of classical parameters that provide understandable information regarding normal and properly functioning pulmonary systems for healthy individuals. In addition, the present invention can also be used to provide further accuracy in these established averages, and to refine them to the point where the normals for pulmonary systems of healthy individuals can be accurately plotted and charted, and then when a potentially diseased lung of a test patient is detected by comparing the latter's test results to the predicted, any divergence can be used to determine the degree of normalcy of the patient, with the discrepancy from the normal providing the physician with more sensitive information that can be analyzed for discerning just where the incipient disease may be germinating.

The present invention lends itself well to the accurate measuring of both the closing volume and nitrogen content of the pulmonary system, and is also adaptable for making other measurements in the category of vital capacity and forced vital capacity, in addition to related respiratory tests.

The invention utilizes the teachings of Poiseuille's law, wherein the velocity of a flow of a fluid through a tube varies directly with the pressure and diameter of the tube and inversely with the tube length and fluid viscosity. This invention utilizes an additional element by including a suspended diaphragm in the path of breath flow and subjecting its physical displacement to accurate detection for a determination of vital information pertaining to lung capacity and function.

The partial diaphragm of this invention includes a foraminous like screen that is suspended within the interior of a flow tube, and which screen can be deflected by the movement of the patient breath therethrough, which lineal deflection may be in the vicinity of one hundred thousandths of an inch, more or less. In the preferred embodiment, the screen further incorporates ferromagnetic means, such as rings, that may be mounted peripherally of the screen and designed for deflecting in unison with said suspended screen. An electrical detecting means, such as a wound core, but more specifically an E-core, may be packaged within a housing through which the flow tube or transducer may be insertably mounted, and which core, as in the case of the E-core, may incorporate a pair of coils, with one of each coils being arranged spatially to either side of the screen and its rings for equalization in the flow of the magnetic lines of flux generated by the core. Movement of the foraminous screen one way or the other longitudinally of the tube provides a type of lineal displacement that disrupts equality and the continuity of flow of the lines of flux around the core, and through the use of any standard form of electrical detecting means the imbalance in the generated inductance may be readily detected, electronically measured, amplified, converted, and readout as a direct reading for indicating the flow, volume, and other pertinent information pertaining to the breath being respired.

While the foregoing described transducer contemplates a form of peripherally suspended diaphragm within the flow tube, such as through the use of a series of arcuate arms which may extend the distance between both the foraminous plate and the interior of the flow tube, other forms of diaphragm mounts, such as center mounts, may be used for likewise suspending the screen in a quasi-free manner so that it will be directly influenced and lineally deflected by the passage of breath. Such center forms of mounts may include a pair of diametral supports spaced to either side of the screen, mounted within the flow tube a fixed distance apart longitudinally of the flow tube, and incorporate a form of rod means that may cooperate with suspension means for normally holding the foraminous plate under static conditions. But, when breath is forced through the flow tube as during specimen tests, such a plate is free for detectable displacement for providing measurements of medical value to the physician or technician analyzing the pulmonary system of the subject patient.

In addition, various forms of capacitive plate detecting means may be utilized for determining the degree of displacement of the partial diaphragm, and provide a source of measurements that can be converted into pulmonary function information. Such capacitive means may include a pair of capacitor plates, one mounted spatially to either side of the diaphragm, and in cooperation with similar type plates mounted to the diaphragm itself, providing for a direct reading of the capacitive imbalance as lineal displacement due to the force of the passing breath occurs. Once again, any type of standard electrical circuitry may be used for detecting this variation in capacitance, and through simple computation or computer means converting such readings to information regarding lung functioning.

The breath transducer of this invention includes other means for facilitating the quick insertion of the flow tube into its holder, including an indexing tab that provides for proper positioning of said tube, in addition to an annulus that limits the extent of insertion of the flow tube into said holder. Obviously any insertion limiting means is necessary to provide for accuracy in the readout from usage of one flow tube to the next, since the positioning of the E-core, capacitor plates, or any other form of lineal detecting means that measures the degree of displacement of the diaphragm must operate consistently from transducer to transducer.

DESCRIPTION OF THE PREFERRED EMBODIMENT

Figure 1:
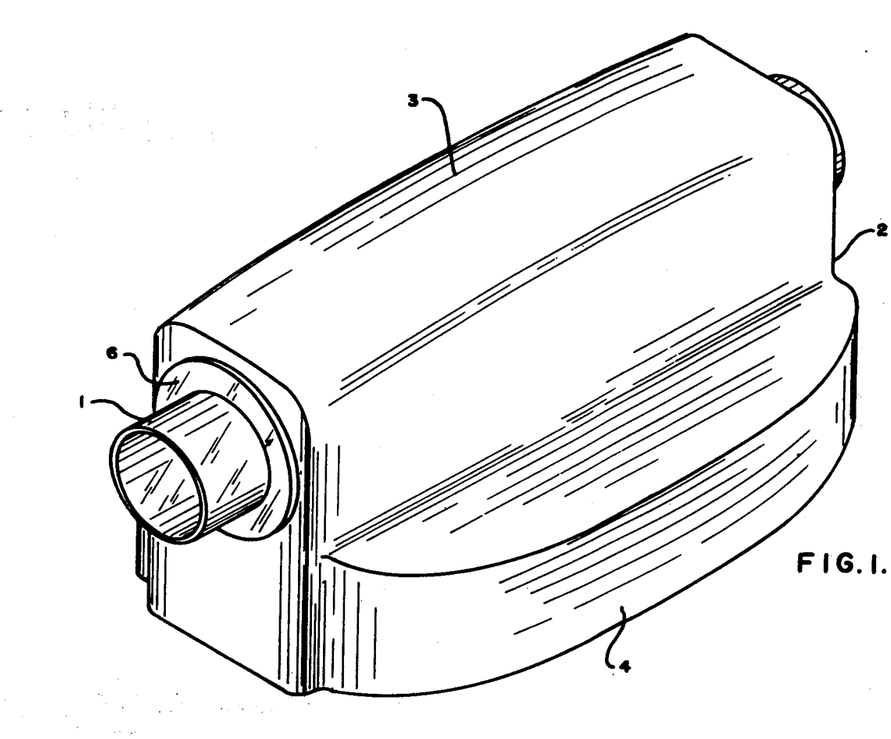
FIG. 1 provides a perspective view of the breath transducer of this invention shown inserted within its holder.

In referring to the drawings, and in particular FIG. 1, there is disclosed the transducer or flow tube 1 of this invention shown mounted by insertion within the housing 2, thereby providing a convenient combination of components that may be easily handled by both the physician and the patient for achieving breath analysis. The transducer 1 may be constructed of any form of polymer, although a transparent material such as methyl methacrylate has been found to be of advantage. In addition, the housing may be constructed of any form of polymer of other material which lends itself to frequent use and handling, while yet maintaining an appearance that is consistent with professional usage. The housing 2 is formed having an upper segment 3 through which is provided longitudinally a series of apertures and through which the transducer 1 may insert, while the lower segment 4 of the housing has smooth curvature flared laterally to facilitate its hand grasping and retention, while interiorly providing ample space for mounting of the various electrical and electronic instrumentalities useful primarily as the means for detecting the functioning of the transducer during usage.

Figure 2:
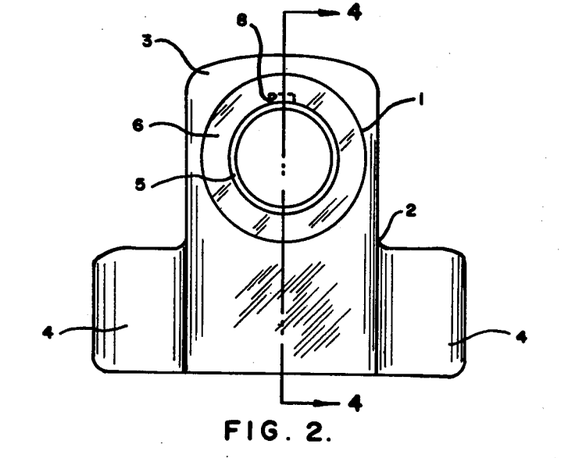
FIG. 2 presents a front end view of the instrument as shown in FIG. 1.
Figure 3:
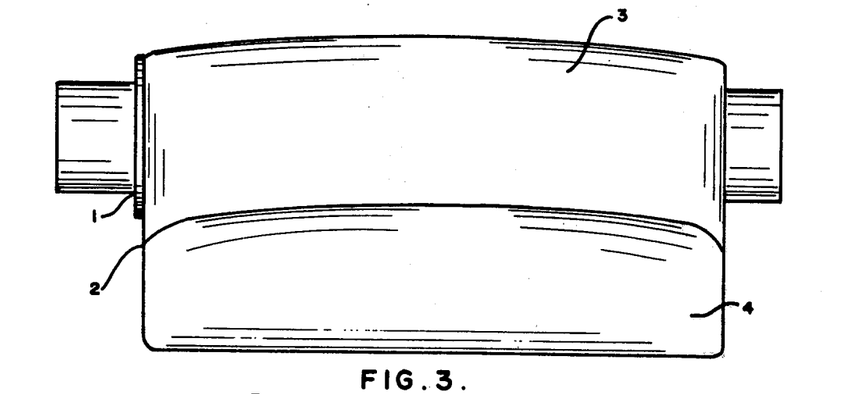
FIG. 3 provides a side view of the instrument shown in FIG. 1.

By referring also to FIGS. 2 and 3, it can be seen that the transducer desirably has sufficient length to provide for its projection from both ends of the housing, but that proximate its one end it is formed to provide the mouthpiece 5 which is normally disposed for oral grasping by the patient, as during pulmonary testing. An annulus 6 is formed integrally with the flow tube, being spaced a slight distance from its one end to form a limit to the length of the mouthpiece 5, while said annulus also circumscribes the depth of insertion of the flow tube into the housing upon its encountering a proximate wall of the upper segment 3 of the housing.

Figure 4:
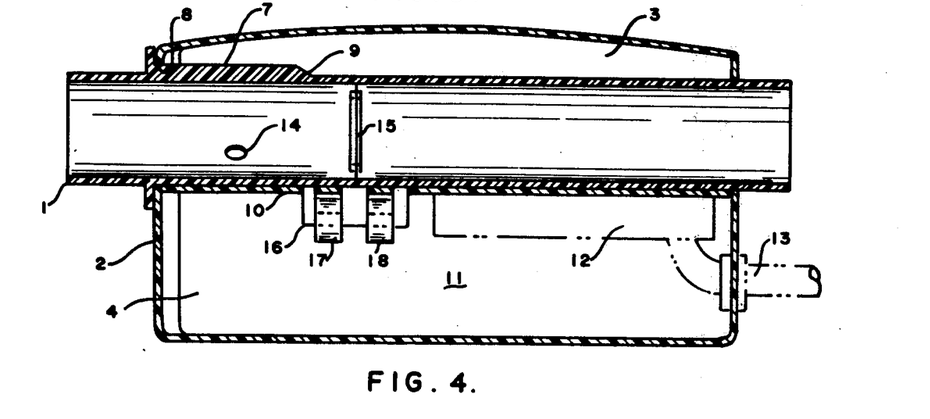
FIG. 4 provides a longitudinal sectional view taken along the line 4—4 of FIG. 2, showing a cross section of the breath transducer and its holder.

By referring also to FIG. 4, in addition to FIG. 2, it can be seen that the transducer 1 includes an indexing means 7, which is in the nature of an integral tab formed upon the surface of the flow tube, with said tab disposed for close contact insertion within a slot 8 formed through the front wall of the housing segment 3, and in this manner provides a means for insuring that the transducer is properly positioned for accurate usage in the housing 2. The front end 9 of the index tab 7 is conveniently tapered to facilitate its initial insertion into the said housing and its formed slot 8.

As further seen in FIG. 4, the housing 2 is formed into its two sections 3 and 4, as previously described, and may include an intermediate wall 10 for segregating the transducer mounting space, as in the section 3, from the electronic packaging space 11, as provided in the bottom section 4 of the housing. As shown within the interior of this lower section 4 of the housing, the electronic package, which may include the usual circuit board and other solid state or other form of electronic devices may be conveniently mounted, as at 12, to the underside of the partition 10, or may be located at any other convenient position within said lower section 4. The usual conduit 13 may insert through one end of the section 4 for communication with the electrical package 12, and provide necessary connection thereto. And, where the transducer is to be utilized for testing other than the lung dead space component or for their closing volume, as for example in the standard nitrogen washout form of other test, then additional instrumentalities customarily used for this latter type of a test may be disposed within this lower section 4 of the housing, and also communicate exteriorly of the same as through the conduit 13 or others. Where the instrument is to be utilized for this type of a test, an aperture 14 may be provided through the wall of the flow tube 1 to provide the location where the nitrogen laden breath may be exhaled for eventual confinement and measuring of its nitrogen content.

As can further be seen in FIG. 4, a form of diaphragm 15 is suspended within the flow tube of the transducer, and as previously summarized and hereinafter described, is subject to lineal displacement due to the force and pressure of the moving breath there past. One means for detecting this degree of displacement of the diaphragm may comprise a form of electrical core 16, which is precisely mounted to the intermediate wall 10 of the lower section 4 of the housing, and disposed generally equidistant to either side of the transducer diaphragm 15. In this particular instance, the core may comprise an E-core, having a pair of electrically conductive coils 17 and 18 provided thereon, and which may be charged with a reference potential for the purpose of inducing the transfer of the magnetic lines of the flux on a path through the various proximate segments of the E-core, in addition to the surrounding environment, particularly thereabove, and within the influence of the said diaphragm. Generally, and in the preferred embodiment, a reference potential within the vicinity of 10 volts, peak to peak, and within a range of 5kHz frequency has been found useful for this purpose, although other ranges of voltages and frequencies may be useful to provide the same function. As is well known in the art, any for of electrical detecting means for determining the degree of imbalance of the inductances in the two segments of the core may be used for detecting the alternating current output of the core, and which output may be rectified and filtered to provide a direct current output signal that is directly proportional to the displacement of the diaphragm. Obviously this output can be correlated to provide a direct readout of the rate of flow and other characteristics of the sample breath, and can be electronically computed and converted into readings for furnishing a direct observation of these results.

Figures 5, 6, 7:
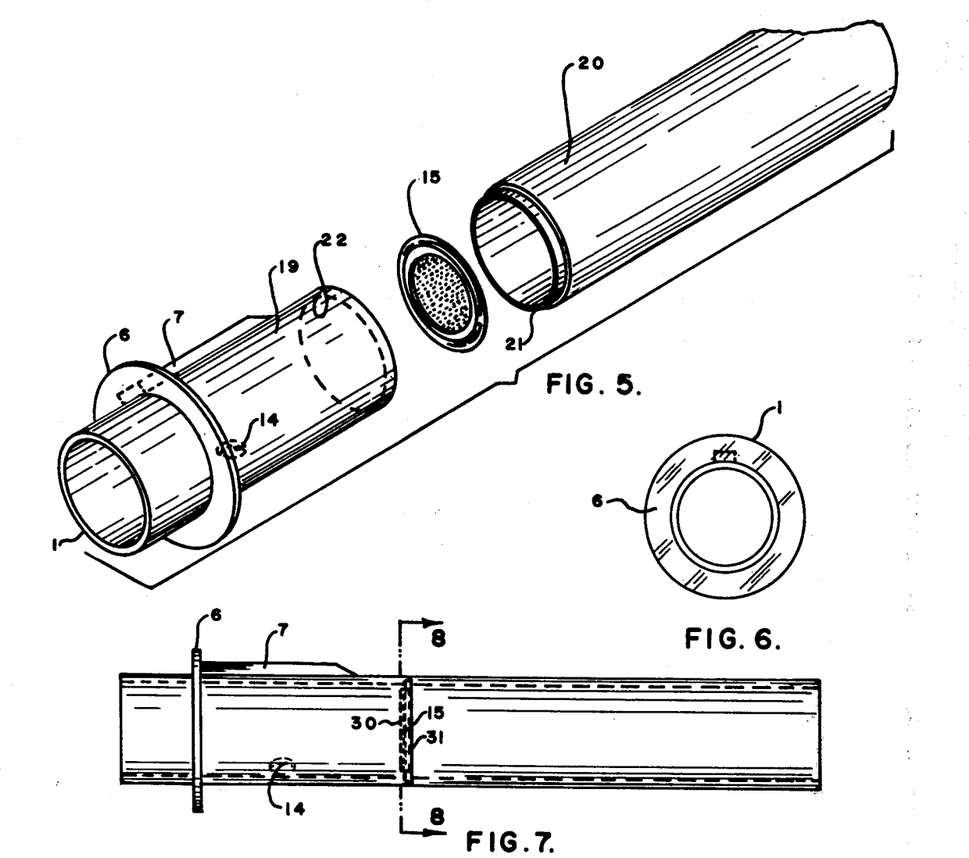
FIG. 5 provides an exploded view of the breath transducer showing its feature to separate as during installation of the diaphragm during manufacture.
FIG. 6 provides and end view showing the mouth piece portion of the breath transducer of this invention.
FIG. 7 provides a side longitudinal view of the breath transducer of this invention.

The preferred style of transducer is shown in FIGS. 5 through 7, wherein the flow tube 1 is shown as being separable into two sections 19 and 20, the site of the separation being approximately at location where the diaphragm 15 mounts therein, so as to facilitate the manufacture of this device. As shown, one end section of the separated flow tube may have a reduced lip 21 that may insert within the mating end 22 of the other tube section, and in this manner provides means for embracing the periphery of the diaphragm 15 therein, with said tube then being adhesively or otherwise secured together to form an integral transducer. Obviously, though, a separable tube is not the only manner for mounting a diaphragm therein.

As previously described, the annulus 6, which acts as a stop means to limit the extent of insertion of the flow tube into its housing, and the index tab 7, are provided integrally upon the flow tube to regulate its precise positioning within the housing, as during usage.

Figure 8:
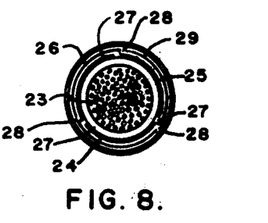
FIG. 8 provides a transverse section taken along the line 8—8 of FIG. 7, showing the diaphragm mounted within the transducer flow tube.

The diaphragm 15 is more accurately shown in FIG. 8, and is formed as a apertured plate 23 useful for partially impeding the flow of breath therethrough so as to induce a slight pressure drop and the incident lineal displacement of the plate under the force of pressure of the breath. This plate may be formed of any type of material that may be reasonably precise and consistent in this degree of displacement with respect to the pressure of the breath it is subjected to, but preferably the plate is constructed of a beryllium copper or perhaps stainless steel, and chemically etched to form uniform apertures therethrough. Preferably the plate will have 200 to 500 mesh openings per square inch. Hence, the completed plate has the appearance of a foraminous screen, which is milled to those precise tolerances so as to provide consistent readout of information under identical test conditions. The foraminous plate 23 has integrally formed therewith, as around its periphery, a series of acruate shaped arms, the three arms 24 through 26 in this particular design, which integrally connect to the plate at one end, as for example as seen at 27, while at their opposite ends, as at 28, they integrally connect with a circumferential ring 29 which is mounted to the interior surface of the flow tube, as for example as previously described with respect to the intermating of the end sections 21 and 22 of the flow tube. On the other hand, many other means for adhesively mounting or adhering the circumferencial ring 29 within the flow tube should be readily apparent. Due to the arcuateness of the arms 24 through 26, it can be seen that the apertured plate 23 is capable of some displacement as pressure is applied to it, which in this particular instance is normally the pressure of the patient's breath, this deflection sometimes achieving a displacement of approximately one hundred thousandths of an inch, an amount which is easily detectable and measurable by the type of previously described electrical pickup and detecting means.

Surrounding the periphery of the apertured plate 23 are a pair of rings, as at 30 and 31, and these rings are secured to the plate at this location by any form of weld or other type of adhesive, and preferably are constructed of ferrous material that provides a more conductive path for transfer of the magnetic lines of flux generated in the E-core. As can be seen, one such ring is mounted to either side of the foraminous plate, and when this partial diaphragm of the transducer is located at the approximate midpoint of the detecting means core, there is provided a balanced relationship between the core inductances indicating a static condition for a null reading. On the other hand, when breath is forced through the transducer and displaces lineally the diaphragm 15, it can be seen that said disphragm will be slightly urged in the direction of breath flow, thereby creating a more conductive path for the lines of flux to flow with respect to one end of the E-core than the other, thereby creating an inductance imbalance which is detectable by the usual electrical circuit means, such as from a center tab associated with the core, as is known in the art. This form of diaphragm may be described as a peripherally mounted displaceable diaphragm.

Figure 9:
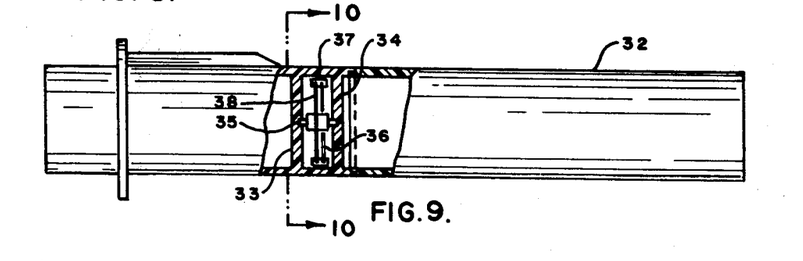
FIG. 9 provides a side view of a modified form of breath transducer, showing in the cutaway portion another form of suspension means for the diaphragm of this invention.
Figure 10:
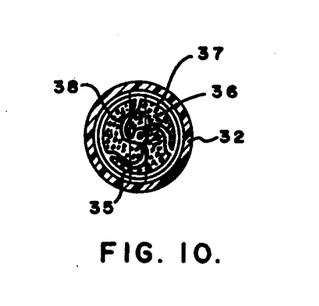
FIG. 10 provides a transverse section taken along the line 10—10 of FIG. 9, showing the modified form of diaphragm and suspension means of its transducer.

As seen in FIGS. 9 and 10, a modified form of the lineal displaceable diaphragm of this invention is shown, and this type of diaphragm is depicted as a centermount form of suspension for the lineally displaceable diaphragm. As shown, the transducer or flow tube 32 has formed integrally therein a pair of spaced apart diametral supports 33 and 34, and which includes a rod member 35 which connects with and spans the longitudinal distance between said two supports. The partial diaphragm 36 is constructed as the type of foraminous screen or plate as previously analyzed with respect to the peripherally mounted diaphragm, but having the rod 35 extending therethrough, and around the periphery of this plate 36 is provided at least one annulus or ring 37. This ring is constructed preferably of a ferro magnetic material, and fuctions similarly to the pair of rings 30 and 31 as previously described with respect to FIG. 7. Connecting between the annulus 37 and the rod member 35 are a series of arcuately shaped arms 38, in this particular instance being three arms, with said arms at their outer ends being secured to the annulus 37, while their inner ends are secured to the rod member 35. Hence, it can be seen that the force of breath flowing through the flow tube 32 will encounter the foraminous plate 36 and cause its displacement. Since this transducer is constructed to the same dimensions that provides for its ease of insertion and location within the housing 2, as previously described, the degree of displacement of the foraminous plate or diaphragm 36 can be gauged by any form of detecting means, such as the E-core 16 as previously described.

Figure 11:
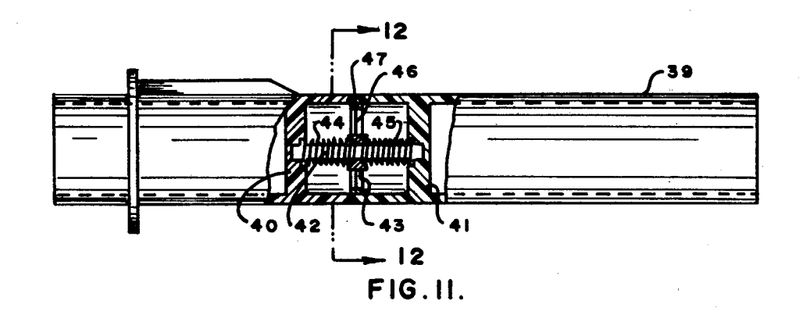
FIG. 11 provides a longitudinal view of the transducer of this invention with a portion being cutaway to disclose a modified form of diaphragm and suspension means.
Figure 12:
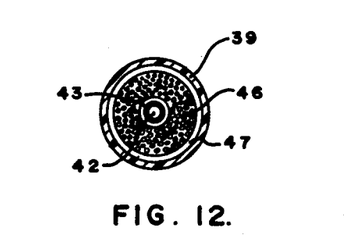
FIG. 12 provides a transverse section taken along the line 12—12 of FIG. 11, showing the modified form of a diaphragm and center mount suspension means therein.

Another modified form of diaphragm suspension, in this particular instance, also comprising a centermount form of suspension, is shown in FIGS. 11 and 12. In this particular embodiment, the transducer or flow tube 39 incorporates the pair of diametral supports 40 and 41, which are arranged a fixed distance apart longitudinally of the flow tube, and spanning the distance between said supports is a rod member 42. Mounted for sliding movement upon said rod member is a sleeve 43, which is conveniently centered upon the rod member by means of a pair of springs 44 and 45, which normally sustain a stationary position for the slidably sleeve as when the transducer is at rest. Extending radially from the sleeve 43 is a foraminous plate or partial diaphragm 46 constructed of the same material and in the same manner as the plates previously described an analyzed. Peripherally mounted circumferentially of said plate in an annulus 47 which is disposed for free sliding movement within the interior of the tube 39. This annulus may comprise a single or a pair of rings, and is preferably constructed of ferrous material so as to provide a more conductive path for the lines of magnetic flux to flow as during usage of the transducer. Once again, the transducer is insertable within a housing as at 2, and a detecting means such as the E-core 16 of FIG. 4, may be used for determining the degree and extent of lineal displacement of the diaphragm during transducer usage. And, as previously described, any inductance imbalance during usage of the transducer can be detected, measured, and converted by electronic means for providing a direct read out corresponding to the rate or volume of flow, or other measurements, characteristic of the specimen breath.

Figure 13:
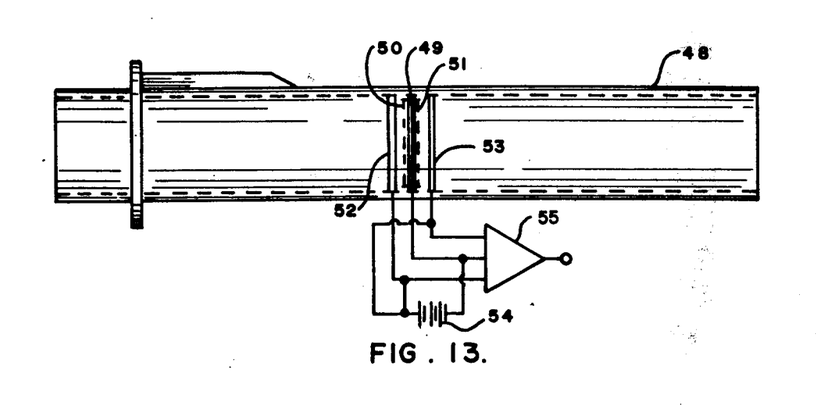
FIG. 13 provides a longitudinal view of the transducer of this invention showing the form of capacitive detecting means for gauging diaphragm displacement.

A final modification or variation upon a type of partial diaphragm and detecting means is shown in FIG. 13. In this embodiment, the transducer or flow tube 48 may incorporate the type of peripherally mounted diaphragm 49 which may be constructed identical with the diaphragm and suspension means 15 as previously analyzed, although the center mount form of suspended diaphragm may also be used in this modified embodiment. In this particular instance, the pair of rings 50 and 51 secure proximate the periphery of the foraminous plate of the diaphragm and function as capacitive plates, and each ring is spaced normally a fixed distance from corresponding capacitive plates 52 and 53 which are also secured rigidly to either the interior of the flow tube, as shown in the drawing, or even can be permanently mounted to the housing and disposed for accommodation of the flow tube therethrough. Actually, these capacitive plates 52 and 53 are also constructed in the form of rings. Hence, a charge, as from a battery or other electrical source 54, provides for charging of the respective pairs of plates 50 and 52, and 51 and 53, so that when the diaphragm 46 is maintained stationary an equal distance between the two plates 52 and 53, there will be no capacitive imbalance that is detectable of any measurement. On the other hand, as specimen breath flows through the transducer, thereby causing the diaphragm 49 to lineally displace, its associated capacitive rings 50 and 51 are likewise displaced providing for this capacitive imbalance being detected, measured, and amplified, as at 55, to provide a readout of information corresponding to the flow of the patient's breath.

It should also be obvious that the principles of this invention can be adapted for use in detecting information about fluid or gas flow in industrial processes.

The foregoing provides a description generally of various types of sensitive means for analyzing breath flow, particularly through the lineal displacement of a diaphragm along the longitudinal length of a transducer, which detected information can be converted for readout of pulmonary function information. Such information can be analyzed by the physician or technician as an indicator of early warning of lung disease. Furthermore, the integral formation of the transducer of this invention, apart from the detecting means, allows its once use and then disposal. Such provides great sanitation in the use of this medical instrument. In addition it is likely that the detecting means may be optically operative, such as through the use of light sensitive diodes, and detect the displacement of the diaphragm in this manner. Variations in the type of embodiments shown and described in this invention may occur to those skilled in the art in light of the foregoing disclosure, and such variations as within the spirit and scope of this invention are intended to be protected by any patent to issue hereon. The description of the preferred embodiment in detail is intended for illustration purposes only.

Having thus described the invention, what is claimed and desired to be secured by Letters Patent is:

1. A diagnostic instrument for use in detecting lung disfunction through specimen breathing and comprising a flow tube means adaptable for accommodating the flow of the breath therethrough, a resiliently mounted diaphragm means disposed within said tube means and subject to lineal displacement due to the force of the moving breath thereby, said diaphragm means comprising a plate means, said plate means having at least one aperture therethrough for allowing the unobstructed passage of the breath there past, said plate means suspended within said flow tube means to provide for its complete and uniform lineal displacement due to the force of the breath moving through the flow tube means, suspension means supporting the plate means within the flow tube means, said suspension means providing for centrally mounting of the said plate means within the said tube means, said suspension means including a pair of supports disposed diametrically across the interior of the tube means and spaced from each other a fixed distance, a rod member extending the distance between and connecting to said supports, said apertured plate means having said rod extending centrally therethrough without obstructing the lineal movement of said plate means with respect to said rod, at least one annulus connecting peripherally of the plate means and in proximity with the inner surface of the flow tube means, a series of resilient arcuate arms interconnecting between said annulus and rod member to provide for suspension of the apertured plate means and its lineal displacement during passage of specimen breath therethrough, and means cooperating with said flow tube means for detecting the degree of lineal displacement of said diaphragm means for providing representative information pertaining to pulmonary functioning for specimen diagnosis.

2. The invention of claim 1 and including a housing provided for accommodating said flow tube means during instrument operation, said housing providing means for facilitating the retention of said flow tube means, said housing having a passage therein through which the flow tube means is removably inserted, said housing containing the detecting means for cooperating with the tube means for determining the degree of lineal displacement of the apertured plate means and providing representative information pertaining to pulmonary functioning for specimen diagnosis.

3. The invention of claim 2 wherein the detecting means comprises an electrically operative means.

4. The invention of claim 3 wherein said annulus is designed for cooperating with the detecting means for determining the degree of lineal displacement of the apertured plate means during passage of breath therethrough, said annulus being made of magnetic flux transferring material, said electrical operational means comprising a core and associated coil capable of conducting a reference current therethrough, the displacement of the plate means and annulus by the passage of specimen breath influencing the inductance resulting from the current flow in the coil thereby providing information decipherable into pulmonary functioning for specimen diagnosis.

5. The invention of claim 4 wherein said core comprises an E-core having a pair of coils provided thereon, with each said coil capable of conducting a current therethrough, the passage of the generated inductances resulting from the change in each coil being influenced by the displacement and location of the plate means and annulus and providing information decipherable into pulmonary functioning for specimen diagnosis.

6. A diagnostic instrument for use in detecting lung disfunction through specimen breathing and comprising a flow tube means adaptable for accommodating the flow of breath therethrough, a resiliently mounted diaphragm means disposed within said tube means subject to lineal displacement due to the force of the moving breath therein, said diaphragm means comprises a plate means, said plate means having at least one aperture therethrough for allowing the unobstructed passage of breath there past, suspension means supporting the plate means within the flow tube means to provide for its complete and uniform lineal displacement due to the force of the breath moving through the flow tube means, said suspension means providing for central mounting of said plate means within the said tube means, said suspension means including a pair of supports disposed diametrically across the interior of the flow tube means and being spaced from each other a fixed distance, a rod member extending the distance between and connecting to the said supports, said apertured plate means having a central aperture provided therethrough, a sleeve connecting to the plate means axially of its centrally disposed aperture, said rod extending through the said sleeve without obstructing the lineal displacement of said plate means and sleeve with respect to the flow tube means, spring means provided upon said rod for normally retaining said plate means and sleeve stationary but allowing for their lineal displacement during passage of specimen breath therethrough, at least one annulus connecting peripherally of the plate means and in proximity with the inner surface of the flow tube means, and detecting means cooperating with said flow tube means annulus for detecting the degree of lineal displacement of said diaphragm means for providing the representative information pertaining to pulmonary functioning for specimen diagnosis.

7. The invention of claim 6 and including a housing provided for accommodating said flow tube means during instrument operation, said housing providing means for facilitating the retention of said flow tube means, said housing having a passage therein through which the flow tube means is removably inserted, said housing containing the detecting means for cooperating with the tube means for determining the degree of lineal displacement of the apertured plate means and providing representative information pertaining to pulmonary functioning for specimen diagnosis.

8. The invention of claim 6 wherein the detecting means comprises an electrically operative means.

9. The invention of claim 8 wherein said annulus is designed for cooperating with the detecting means for determining the degree of lineal displacement of the plate means during passage of breath therethrough, said annulus being made of magnetic flux transferring material, said electrical operative means comprising a core and associated coil capable of conducting a reference current therethrough, the displacement of the plate means and annulus by the passage of specimen breath influencing the inductance resulting from the current flow in the coil thereby providing information decipherable to pulmonary functioning for specimen diagnosis.

10. The invention of claim 9 wherein said core comprises an E-core having a pair of coils provided thereon, with each said coil capable of conducting a charge therethrough, the passage of the generated inductances resulting from the charge in each coil being influenced by the displacement and location of the plate means and its associated annulus and providing information decipherable into pulmonary functioning for specimen diagnosis.

11. A diagnostic instrument for use in detecting lung disfunction through specimen breathing and comprising a flow tube means adaptable for accommodating the flow of breath therethrough, a resiliently mounted diaphragm means disposed within said tube means subject to lineal displacement due to the force of the moving breath thereby, said diaphragm means comprising a plate means, said plate means having at least one aperture therethrough for allowing the unobstructed passage of breath there past, said plate means being suspended within said flow tube means to provide for its complete and uniform lineal displacement due to the force of the breath moving through the flow tube means, detecting means cooperating with said flow tube means for detecting the degree of lineal displacement of said diaphragm means, said detecting means comprising an electrically operative means, said apertured plate means having first and second capacitive means mounted peripherally of said plate means and on opposite sides thereto and provided for displacing therewith, a pair of additional capacitive means fixedly mounted within said flow tube means and provided normally a set distance from said first and second capacitive means and apertured plate means, means for charging certain of said capacitive means, and said detecting means including means for detecting any capacitive imbalance between the charged capacitive means upon displacement of said first and second capacitive means and its apertured plate means during passage of specimen breath therethrough for providing representative information pertaining to pulmonary functioning for specimen diagnosis.

* * * * *